United States Patent [19]

Woo et al.

[11] Patent Number: 5,552,471

[45] Date of Patent: Sep. 3, 1996

[54] SOLID SUPPORT REAGENTS FOR THE SYNTHESIS OF 3'-NITROGEN CONTAINING POLYNUCLEOTIDES

[75] Inventors: Sam L. Woo, Redwood City; Steven Fung, Palo Alto, both of Calif.

[73] Assignee: The Perkin-Elmer Corporation, Foster City, Calif.

[21] Appl. No.: 293,637

[22] Filed: Aug. 17, 1994

[51] Int. Cl.$^6$ .............. C03C 12/00; C08L 25/06; C07H 21/04

[52] U.S. Cl. .............. 524/494; 524/492; 524/493; 525/155; 525/326.1; 525/333.5; 525/333.6; 536/25.3

[58] Field of Search .............. 536/25.3; 501/33; 524/346, 492, 493, 494; 525/155, 326.1, 333.5, 333.6

[56] References Cited

U.S. PATENT DOCUMENTS

| | | | |
|---|---|---|---|
| 4,415,732 | 11/1983 | Caruthers et al. | 536/25.34 |
| 4,458,066 | 7/1984 | Caruthers et al. | 536/25.34 |
| 4,908,405 | 3/1990 | Bayer et al. | 525/61 |
| 5,141,813 | 8/1992 | Nelson | 536/24.3 |
| 5,380,833 | 1/1995 | Urdea et al. | 536/22.1 |
| 5,401,837 | 3/1995 | Nelson | 536/25.32 |

OTHER PUBLICATIONS

Asseline et al., Tetrahedron Letters, 48(7): 1233–1254 (1992), Solid–Phase Preparation of 5',3'–Heterobifunctional Oligodeoxyribonucleotides Using Modified Solid Supports.
Polymers and Polyoxyethylene, Process for Their Production, and Their Usage.
Nelson et al., Nucleic Acids Research, 17(18): 7187–7194 (1989), Bifunctional Oligonucleotide Probes Synthesized Using a Novel CPG Support are Able to Detect Single Base Pair Mutations.
Asseline et al., Tetrahedron Letters, 31(1): 81–84 (1990), New Solid–Phase for Automated Synthesis of Oligonucleotides Containing an Amino–Alkyl Linker at Their 3'–End.
Petrie et al., Bioconjugate Chemistry, 3: 85–87 (1992), An Improved CPG Support for the Synthesis of 3'–amine–tailed Oligonucleotides.
Nelson et al., Nucleic Acids Research, 20(23): 6253–6259 (1992), Oligonucleotide Labeling methods 3. Direct Labeling of Oligonucleotides Employing a Novel, non–nucleosidic, 2–aminobutyl–1,3–propanediol Backbone.
Thaden et al., Bioconjgate Chemistry, 4: 395–401 (1993), Automated Synthesis of Oligodeoxyribonucleoside Methylphosphonates having [N–(3–aminoprop–1–yl)–N–(2–hydroxyethyl)–2aminoethyl] Phosphate or Methylphosphonic Acid at the 3'End using a Modified Controlled Pore Glass Support.
Gryaznov et al., Tetrahedron Letters,34(8): 1261–1264 (1993), Anchor for One Step Release of 3'–Aminooligonucleotides from a Solid Support.
Hovinen et al., Tetrahedron Letters, 34(50): 8169–8172 (1993), Synthesis of 3'–Functionalized Oligonucleotides on a Single Solid Support.
Hovinen et al., Tetrahedron Letters, 34(32): 5163–5166(1993), A New Method to Prepare 3'Modified Oligonucleotides.
Caruthers et al., Genetic Engineering, 4: 1–17 (1982), New Methods for Synthesizing Deoxyoligonucleotides.
Applied Biosystems, Users Manual Model 392 and 394 DNA Synthesizers, pp. 6–1 through 6–22, Applied Biosystems, Part No. 901237 (1991), Users Mannual Model 392 and 394 DNA Synthesizers.
Agrawal ed., Protocols for Oligonucleotide Conjugates, pp. 93–120, Humana Press, Totowa, NJ (1994).
Gait ed., Oligonucleotide Synthesis, pp. 45–49, IRL Press, Washington, DC (1984).
Wright et al., Tet. Lett., 34: 3373–3376 (1993), Large Scale Synthesis of Oligonucleotides via Phosphoramidite Nucleosides and a High–loaded Polystyrene Support.
Applied Biosystems Research News, Model 390Z, Feb. 1994, High–Loaded Polystyrene(HLP™) Supports for Large–Scale Oligonucleotide Synthesis on the Model 390Z Synthesizer.
Gao et al., Tetrahedran Lett., 32(40): 5477–5480 (1991), H–Phosphonate Oligonucleotide Synthesis On a Polyethylene Glycol/Polystyrene Copolymer.

*Primary Examiner*—Gary L. Kunz
*Attorney, Agent, or Firm*—Paul D. Grossman

[57] ABSTRACT

The compounds are exemplified by the class of sulfoethyl oxygen-substituted carbamates, such compounds being useful as support reagents for automated polynucleotide synthesis of 3'-nitrogen functionalized polynucleotides. The invention includes, in one aspect, a polynucleotide synthesis reagent having the structure:

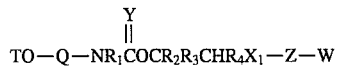

where T is an acid-cleavable hydroxyl protecting group, e.g., 4,4'-dimethoxytritil; Q is a linker connecting the nitrogen and oxygen, e.g., n-hexyl; $R_1$ is a nitrogen substituent, e.g., hydrogen; $R_2$ through $R_4$ are separately hydrogen or lower alkyl; Y is an atom which is electronegative with respect to carbon, e.g., oxygen or sulfur; $X_1$ is an atom which is electronegative with respect to carbon, e.g., sulfone; Z is a bond or spacer arm, e.g., ethylsuccinate; and W is a derivatized solid synthesis support capable of linking to Z, e.g., an amino-dirivitized controlled pore glass. In a second aspect, the present invention includes a polynucleotide synthesis reagent having the structure:

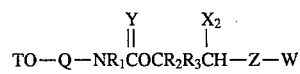

where T, Q, $R_1$, $R_2$–$R_3$, $X_2$, Z, and W are as defined above.

26 Claims, No Drawings

SOLID SUPPORT REAGENTS FOR THE SYNTHESIS OF 3'-NITROGEN CONTAINING POLYNUCLEOTIDES

BACKGROUND

This invention relates generally to solid support reagents used for the synthesis of functionalized polynucleotides, and more particularly, to the synthesis of polynucleotides having a nitrogen atom located at the 3'-end.

The continued rapid development of non-isotopic polynucleotide probes, DNA/RNA amplification methods, and bioactive antisense and triplex synthetic reagents, has greatly increased the demand for chemically modified polynucleotides. One popular approach to polynucleotide modification is to introduce a primary aliphatic amine to one end of the polynucleotide, thereby making it possible to readily functionalize the polynucleotide with substituents containing electrophilic moieties, e.g., isothiocyanates or activated esters. Common substituents include fluorophores, enzymes, biotin, intercalators, cross-linkers, nucleic acid cleaving reagents, modifiers of cellular uptake, and the like.

The most effective and convenient method for the introduction of an nitrogen atom to an end of a synthetic polynucleotide is to use an appropriately fuctionalized synthesis support followed by selective cleavage of the nitrogen-functionalized polynucleotide from that support. A number of methods currently exist for synthesizing 3'-nitrogen functionalized polynucleotides using modified supports, however, all of these methods produce a racemic mixture of products and/or require non-standard automated polynucleotide synthesis reagents and/or procedures, thereby complicating the purification and/or synthesis of these compounds.

For the foregoing reasons, there is a need for a solid support reagent capable of synthesizing 3'-nitrogen functionalized polynucleotides in non-racemic preparations using standard polynucleotide synthesis reagents, systems and procedures. More specifically, a modified solid support which is stable to (i) polynucleotide synthesis capping reagents such as acetic anhydride and pyridine, (ii) oxidants such as iodine, (iii) medium-strength acids such as trichloroacetic acid, and (iv) phosphorylating agents such as phosphoramidites; while at the same time being labile to typical polynucleotide synthesis cleavage reagents such as ammonium hydroxide.

SUMMARY

The present invention is directed toward our discovery of a polynucleotide synthesis support for use in automated polynucleotide synthesis that is useful for synthesizing 3'-nitrogen functionalized polynucleotides.

It is an object of the invention to provide a solid support reagent that is capable of supporting the synthesis of polynucleotides in non-racemic preparations using standard polynucleotide synthesis reagents, systems and procedures.

The present invention includes, in one aspect, a polynucleotide synthesis reagent comprising a compound of the formula:

where the variable elements of the above formula are defined as follows: T is an acid-cleavable hydroxyl protecting group; Q is a linker connecting the nitrogen and oxygen; $R_1$ is an inert nitrogen substituent; $R_2$ through $R_4$ are separately hydrogen or lower alkyl; Y is an atom which is electronegative with respect to carbon; $X_1$ is an atom which is electronegative with respect to carbon; Z is a bond or spacer arm; and W is a derivatized solid synthesis support capable of joining to Z.

In a second aspect, the present invention includes a polynucleotide synthesis reagent comprising a compound of the formula:

$$TO-Q-NR_1COCR_2R_3CH-Z-W$$
with Y (double bond) above NR₁CO carbon and $X_2$ above CH where the variable elements of the above formula are defined as follows: T is an acid-cleavable hydroxyl protecting group; Q is a linker connecting the nitrogen and oxygen; $R_1$ is an inert nitrogen substituent; $R_2$ through $R_4$ are separately hydrogen or lower alkyl; Y is an atom which is electronegative with respect to carbon; $X_2$ is an atom which is electronegative with respect to carbon; Z is a bond or spacer arm; W is a solid synthesis support capable of joining to Z.

In one preferred embodiment of either aspect, T is 4,4'-dimethoxytrityl, monomethoxytrityl, α-naphthyldiphenylmethyl, or tri(p-methoxyphenyl)methyl. More preferably, T is 4,4'-dimethoxytrityl.

In another preferred embodiment of either aspect, Q is lower alkyl, lower alkylene oxide, or, amide, carbamate, sulfonamide, or urea when in combination with a nitrogen of the solid support reagent, or any combination thereof. More preferably, Q is lower alkyl or lower alkylene oxide.

In yet another preferred embodiment of either aspect, $R_2$ through $R_4$ are hydrogen.

In another preferred embodiment of either aspect, Y is oxygen or sulfur. More preferably, Y is oxygen.

In a preferred embodiment of the first aspect of the invention, $X_1$ is sulphonyl, carbonyl, sulfoxide, perfluoro lower alkyl, or sulfonyl-, carbonyl-, sulfoxide-, nitro-, cyano-, or perfluoro lower alkyl-substituted aryl. More preferably, $X_1$ is sulphonyl, carbonyl, sulfoxide.

In a preferred embodiment of the second aspect of the invention, $X_2$ is sulphonyl, carbonyl, sulfoxide, cyano, perfluoro lower alkyl, or sulfonyl-, carbonyl-, sulfoxide-, nitro-, cyano-, or perfluoro lower alkyl-substituted aryl. More preferably, $X_2$ is sulphonyl, carbonyl, or cyano.

In another preferred embodiment of either aspect, Z is, in combination with a terminal nitrogen of the solid synthesis support derivatized with a nitrogen-terminated linker, carbamate, urea, amide, sulfonamide, or a group of the formula:

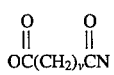

wherein v is between 0 and 20.

In another preferred embodiment of either aspect, W is CPG derivatized with an amino-terminated linker.

In a final preferred embodiment of either aspect, W is porous polystyrene derivatized with an amino-terminated linker.

In a preferred embodiment of the first aspect, the polynucleotide synthesis reagent is a compound of the formula

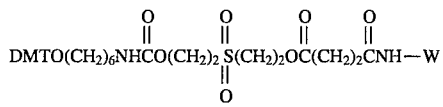

In a preferred embodiment of the second aspect, the polynucleotide synthesis reagent is a compound of the formula

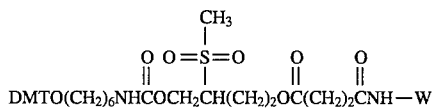

where in both of the above structures, T is 4,4'-dimethoxytrityl (DMT), Q is n-hexyl, $R_1$–$R_4$ is hydrogen, Y is oxygen, $X_1$ (or $X_2$) is sulfonyl, Z is an ethyl succinate linker, and W is an amino derivatized solid support.

In a third aspect, the present invention includes a method for the synthesis of polynucleotides containing a 3'-nitrogen atom using the solid supports of the present invention. The synthesis takes place on a solid support reagent having the formula:

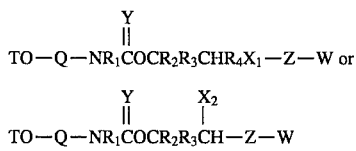

where, T is an acid-cleavable hydroxyl protecting group; Q is a linker for connecting nitrogen and oxygen; $R_1$ is a nitrogen substituent; $R_2$ through $R_4$ are separately hydrogen or lower alkyl; Y is an atom which is electronegative with respect to carbon; $X_1$ is an atom which is electronegative with respect to carbon; $X_2$ is an atom which is electronegative with respect to carbon; Z is a bond or spacer arm; and W is a derivatized solid synthesis support capable of linking to Z. Next, the solid support is treated with acid to remove the acid-cleavable hydroxyl protecting group. A protected nucleoside monomer is then added along with a weak acid, forming a linkage between the nucleoside and the growing support-bound chain. The unreacted sites on the solid support are then capped with a capping reagent and oxidizing reagents are added. The above steps are the repeated until the polynucleotide chain elongation is complete. At this point, the oligonucleotide is still bound to the solid support with protecting groups on the phosphates and the exocyclic amines of the bases. The oligonucleotide is cleaved from the support by treatment with concentrated ammonium hydroxide, and the protecting groups are removed by treating the crude DNA solution in ammonium hydroxide at an elevated temperature, e.g., 55° C.

DESCRIPTION

I. DEFINITIONS:

The term "lower alkyl" as used herein denotes straight-chain, branched-chain, and cyclized alkyl groups containing from 1 to 8 carbon atoms.

The term "lower alkylene oxide" as used herein denotes straight-chain, branched-chain, and cyclized alkylene oxide groups containing from 2 to 8 carbon atoms, e.g., polyethylene oxide.

The term "electron withdrawing" denotes the tendency of a substituent to attract valence electrons from neighboring atoms, i.e., the substituent is electronegative with respect to neighboring atoms. One popular and well accepted index of electronegativity is the Pauling index.

II. DETAILED DESCRIPTION:

Reference will now be made in detail to the preferred embodiments of the invention. While the invention will be described in conjunction with the preferred embodiments, it will be understood that they are not intended to limit the invention to these embodiments. On the contrary, the invention is intended to cover alternatives, modifications, and equivalents, which may be included within the invention as defined by the appended claims.

In a first preferred embodiment, the solid support of the present invention is defined by the formula:

FORMULA I

where T refers generally to an acid-cleavable hydroxyl protecting group. Preferably, T is the triphenylmethyl radical and its electron-donating-substituted derivatives, where, as used herein, the term "electron-donating" denotes the tendency of a substituent to release valence electrons to neighboring atoms in the molecule of which it is a part, i.e., it is electropositive with respect to neighboring atoms in the molecule. Preferably, electron-donating substituents include amino, lower alkyl having between 1 and 8 carbon atoms, lower aryl having between 1 and 8 carbon atoms, alkoxy having from 1 to 8 carbon atoms, and the like. More preferably, the electron-donating substituents are methoxy. Exemplary trityls include 4,4'-dimethoxytrityl (i.e. bis(p-anisyl)phenylmethyl), monomethoxytrityl, α-naphthyl-diphenylmethyl, tri(p-methoxyphenyl)methyl, and the like. Attachment and cleavage conditions for these and other trityls can be found in Greene and Wuts, Protective Groups in Organic Synthesis, 2nd Edition (John Wiley, New York, 1991).

Q is a linker which, when the 3'-nitrogen-functionalized oligonucleotide is cleaved from the support, serves to link the 3'-nitrogen with the oligonucleotide through an oxygen. In some cases, Q also serves to provide a degree of spatial separation between the oligonucleotide and the 3'-nitrogen, e.g., to increase the reactivity of the 3'-nitrogen by reducing the steric hindrance caused by the oligonucleotide. Finally, Q may add functionality to the 3'-nitrogen oligonucleotide such as enhanced nuclease resistance, solubility, transport properties, hybridization, altered electrophoretic mobility, and the like. Q should be stable to typical DNA synthesis reagents. Because Q is not a central feature of the invention and provides a generic function, it will be appreciated that Q can have a wide variety of forms. Preferably, Q is lower alkyl, lower alkylene oxide, or, amide, carbamate, sulfonamide, or urea when in combination with a nitrogen of the solid support reagent, or any combination thereof. More preferably, Q is lower alkyl or lower alkylene oxide.

$R_1$ is a nitrogen substituent which can vary greatly depending on the nature of the desired final product. It will be appreciated that because $R_1$ is not a central feature of the invention and provides a generic function, $R_1$ can have a wide variety of forms. $R_1$ is chosen so that the bonded nitrogen atom is chemically stable during synthesis and subsequent to oligonucleotide cleavage. Preferably, $R_1$ is stable to standard polynucleotide synthesis reagents and does not interfere with the elimination of the Y=C=O group during polynucleotide cleavage. If a reactive amino group is desired subsequent to polynucleotide cleavage, $R_1$ should not substantially interfere with the nitrogen reactivity. In this case, $R_1$ is preferably lower alkyl or hydrogen. Most preferably, $R_1$ is hydrogen.

If a reactive amino group is not required in the final product, $R_1$ need only be stable to standard polynucleotide synthesis chemistry and not interfere with the elimination of the Y=C=O group during polynucleotide cleavage. Preferably, $R_1$ is lower alkylene oxide, hydrogen, alkyl, sulfonyl, acyl, alkoxycarbonyl, or carbamoyl. Alternatively, $R_1$ is a functional moiety such as a dye, specific binding reagent, a transport-enhancing reagent, e.g., cholesterol, and the like.

Y is a functionality which serves to polarize the double bond between itself and the bonded carbon such that the bonded carbon is made electropositive, thereby favoring the elimination of a Y=C=O group upon base-cleavage from the support. Preferably Y is electronegative with respect to carbon. Preferably, Y is either oxygen or sulfur. More preferably, Y is oxygen.

$X_1$ is an electron withdrawing functionality which serves to make a hydrogen which is bonded to the same carbon as $X_1$ acidic, i.e., pKa between 15 and 35, thereby facilitating elimination by ammonia. Preferably, $X_1$ is sulphonyl, carbonyl, sulfoxide, perfluoro lower alkyl, or sulfonyl-, carbonyl-, sulfoxide-, nitro-, cyano-, or perfluoro lower alkyl-substituted aryl. More preferably, $X_1$ is sulphonyl, carbonyl, or sulfoxide.

Z is a bond or spacer arm which serves to link the solid support and the functional regions of the invention. In many instances, Z also serves to provide spatial separation between the solid support and the functional regions of the invention in order to eliminate the transport resistances associated with solid phase synthesis, i.e., to allow the oligonucleotide synthesis to proceed with liquid-phase kinetics. Z should be stable to typical DNA synthesis reagents. Preferably, Z is, in combination with the terminal nitrogen of the derivatized solid synthesis support, carbamate, urea, amide, sulfonamide, or a group of the formula:

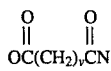

where v is an integer between 0 and 20.

$R_2$ through $R_4$ are chosen so as to form a stable spacer between chemically active portions of the support. Preferably, $R_2$ through $R_4$ each taken separately represent hydrogen or lower alkyl. More preferably, $R_2$ through $R_4$ taken separately each represent hydrogens.

W is a derivatized solid substrate on which the polynucleotide synthesis takes place. W can have a variety of forms and compositions, however, the solid substrate should: (i) be substantially insoluble in the reaction solvents (ii) be chemically stable to standard polynucleotide synthesis reagents, (iii) be capable of chemical derivitization, (iv) provide the desired oligonucleotide loading, (v) have adequate compression strength to withstand elevated pressure encountered during processing, and, (vi) be available in a desirable particle size range and distribution. Furthermore, W is derivatized in order to facilitate attachment of the oligonucleotide to the support.

In one preferred embodiment, W is an inorganic polymer support. A wide variety of inorganic polymers can be employed in the present invention and these include, for example, silica, porous glass, aluminosilicates, borosilicates, metal oxides such as alumina and nickel oxide, various clays, and the like. Preferably, the inorganic solid substrate is controlled pore glass (CPG). Controlled pore glass consists of uniformly milled and screened particles of almost pure silica that are honeycombed with pores of a controlled size. It is manufactured from a borosilicate material that has been specially heat treated to separated the borates from the silicates. The pores are formed by removing the borates by an acidic etching process, their size being dependent on the nature of the heating process. More preferably, the CPG is in the form of 150 µm diameter particles having 500 Å pores, e.g., Users Manual Model 392 and 394 polynucleotide Synthesizers, pages 6-5 through 6-9, Applied Biosystems, Ver. 2.00, Doc. Rev. A, Part No. 902351 (1992).

Derivatization of CPG supports with amino-terminated linkers is well known in the art of polynucleotide synthesis, e.g., Gait, Editor, Oligonucleotide Synthesis, pages 45–49 (IRL Press, 1984), and in fact, CPG beads derivatized with an alkyl amine having a primary amino loading of about 100 mmol/g are commercially available (Pierce Chemical Company, Rockford, Ill.). Briefly, in the case of alkyl amino substrates, a suspension of CPG particles is reacted with an aminoalkyltrimethoxysilane reagent, filtered, and dried.

A second preferred solid substrate is non-swellable porous polystyrene. As used herein, "non-swellable" means that the porous polystyrene material remains substantially mechanically rigid, in particular, does not appreciably increase in volume, when exposed to solvents, reactants and products of the phosphoramidite and/or hydrogen phosphonate polynucleotide synthesis chemistries. As used herein, "porous" means that the non-swellable polystyrene contains pores having substantially uniform diameters in the range of between 100 and 4000 Å.

The polystyrene support is amino-derivatized by standard procedures, e.g., Wallace et al., pages 638–639 in Scouten ed., *Solid Phase Biochemistry* (John Wiley & Sons, 1980); Wright et al. Tet. Lett., 34: 3373–3376 (1993); Bayer et al, U.S. Pat. No. 4,908,405; Applied Biosystems Research News, Model 390Z, February 1994. Briefly, hydroxymethylpthalimide is reacted with the polystyrene support with a catalytic amount of methylsulfonic acid to form pthalimidomethyl polystyrene. This material is then treated with hydrazine to remove the pthalimide protecting group to give aminomethylated polystyrene. Typically, the amino loading varies from 20 to 60 µmoles of amino functionality per gram of non-swellable porous polystyrene. The loading level can be controlled by adjusting the concentrations of the reagents and reaction times.

A recently developed alternative polystyrene derivatizing chemistry replaces the terminal amino group with a free hydroxyl group by attaching several polyoxyethylene residues or chains having free hydroxyl groups available for coupling with the polynucleotide, e.g., Bayer and Rapp, U.S. Pat. No. 4,908,405; Gao et al., Tetrahedron Lett., 32(40):5477–5480 (1991).

In a third preferred embodiment, W is a non-polystyrene organic polymer. The polymer support can be derived from naturally occurring materials which are synthetically modified, and synthetic materials. Of particular interest are polysaccharides, particularly crosslinked polysaccharides, such as agarose, which is available as Sepharose™, dextran, which is available as Sephadex™, cellulose, starch, and the like (Sepharose™ and Sephadex™ being trademarked products of Pharmacia Fine Chemicals, Piscataway, N.J.). Other materials include polyacrylamides, polyvinyl alcohols, silicones, Teflons™, and the like.

In a second preferred embodiment, the solid support of the present invention is defined by the formula:

$$\text{TO—Q—NR}_1\overset{\overset{Y}{\|}}{\text{C}}\text{OCR}_2\text{R}_3\overset{\overset{X_2}{|}}{\text{C}}\text{H—Z—W} \quad \text{FORMULA II}$$

wherein $X_2$ is an electron withdrawing functionality which serves to make any hydrogen which is bonded to the same carbon as $X_2$ acidic, thereby facilitating elimination by ammonia. Preferably, $X_2$ is sulphonyl, carbonyl, sulfoxide, cyano, perfluoro lower alkyl, or sulfonyl-, carbonyl-, sulfoxide-, nitro-, cyano-, or perfluoro lower alkyl-substituted aryl. More preferably, $X_2$ is sulfonyl, carbonyl, or cyano.

All other variable elements in the compounds of Formula II are as defined as above in the context of Formula I compounds.

III. GENERAL SYNTHETIC METHOD:

A. Synthesis of the X1-containing solid support of Formula I:

The following is a preferred generalized synthesis method for the compounds of Formula I. Generally, the reaction scheme involves preparing a hydroxyl-protected alcoholamine (T-amine), preparing a hydroxyl-protected carbamatealcohol (T-CA) by reacting a diol with a phosgene equivalent and then the T-amine. The T-CA is then treated to form an active T-CA linker which is reacted with an amino-derivatized solid substrate.

To form the T-amine, first, the amine moiety of an aminoalcohol is protected with a base-labile protecting group. The aminoalcohol (approx. 1.0 equivalent), defined by the formula

HOQNHR$_1$ wherein the variable elements are as indicated above, is dissolved in an organic solvent, e.g., methanol, ether, methylene chloride, and the like, and a base-labile amino protecting reagent (approx. 1.1 equivalents), e.g., ethyltrifluoroacetate, is added dropwise to the aminoalcohol solution at a temperature of between −5° and 25° C., and stirred for between 1–6 hrs at a temperature of between 0° and 40° C., after which the solvent is evaporated under vacuum. Exemplary amino alcohols which are commercially available include aminoethanol, 6-amino-1-hexanol, aminocyclohexanol, 2-(2-aminoethoxy)ethanol, leucinol, and the like. The residue is dissolved in a water-immiscible organic solvent, e.g., methylene chloride, ether, ethylacetate, and the like, washed with water, and dried over sodium sulfate. The solvent is then evaporated under vacuum to give a protected aminoalcohol product.

Next, the alcohol moiety of the protected aminoalcohol is protected. The protected aminoalcohol (approx. 1.0 equivalent) and a tertiary amine (approx. 1.5 equivalents), e.g., diisopropylethylamine, triethylamine, and the like, are dissolved in an aprotic organic solvent, e.g., methylene chloride, ether, and the like, and an acid-labile hydroxyl protecting agent, (approx. 1.1 equivalents), e.g., a tritylating agent such as dimethoxytritylchloride, is added at a temperature of between −10° and +10° C. The mixture is stirred at between 0° and 25° C. for between 5 and 25 hrs, after which it is diluted with an equal volume of the organic solvent used in the reaction. The reaction solution is then washed with a saturated sodium bicarbonate solution, dried over sodium sulfate, and concentrated under vacuum to give a T-protected aminoalcohol.

Finally, the amine moiety of the T-protected aminoalcohol is deprotected by treatment with base. The T-protected aminoalcohol is dissolved in a polar organic solvent, e.g., methanol, a basic aqueous solution, e.g., 4N sodium hydroxide, is added at between 0° and 25° C., and the reaction is stirred at between 25° and 60° C. for between 10 min and 2 hrs. The organic solvent is evaporated under vacuum and the residue is dissolved in a water-immiscible organic solvent, e.g., ethylacetate, ether, and the like, the solution is washed with water, and dried over sodium sulfate. The solvent is evaporated under vacuum to give a T-amine defined by the formula:

TOQNHR$_1$ wherein the variable elements are as indicated above.

To form the T-CA, a dry diol is used having the formula:

HOCR$_2$R$_3$CHR$_4$X$_1$Z'OH wherein Z' is in some cases equivalent to Z, and in other cases is a precursor to Z, depending on the method used to subsequently activate the T-CA. The other variable elements are as indicated above. The dry diol (2 to 10 equivalents) and a tertiary amine (1.0 equivalent), e.g., diisopropylethylamine, are dissolved in an aprotic organic solvent, e.g., pyridine, a phosgene equivalent (1.0 equivalent), e.g., 4-nitrophenylchloroformate, is added between 0° and 25° C., and the solution is stirred at room temperature for between 10 min and 2 hrs. This solution is then added to a solution of the T-amine prepared above (approx. 0.25 to 1 equivalent) along with a tertiary amine (approx. 1.0 equivalent), e.g., diisopropylethylamine, triethylamine, and the like, in an aprotic solvent, e.g., pyridine. The reaction is stirred at between 0° and 25° C. for between 10 min and 2 hrs, the solvent is evaporated under vacuum, the residue is dissolved in a water-immiscible organic solvent, e.g., ethylacetate, washed with water, and dried over sodium sulfate. The solvent is evaporated under vacuum to give a T-carbamate alcohol (T-CA) product defined by the formula:

$$\text{TOQNR}_1\overset{\overset{O}{\|}}{\text{C}}\text{OCR}_2\text{R}_3\text{CHR}_4\text{X}_1\text{Z'OH}$$

wherein the variable elements are as indicated above.

The above T-CA is then converted to an active linker using either one of two preferred procedures. In the first preferred procedure, the T-CA is treated with an amine base, e.g., 4-dimethylaminopyridine, and an anhydride, e.g., succinic anhydride, in an aprotic solvent, e.g., methylene chloride, for between 10 and 60 min at between 10° and 60° C. The solution is washed with a weak aqueous acid, e.g., citric acid, dried over sodium sulfate, and concentrated under vacuum to give a T-carbamate alcohol linker (T-CA linker). The T-CA linker is then activated by treatment with an equimolar solution of 1-hydroxybenzotriazole (HOBT) and 2-(1H-benzotriazol-1-yl)-1,1,3,3,-tetramethyluronium (HBTU) (0.45M solution in N,N-dimethylformamide) in a polar aprotic solvent, e.g., dimethyl formamide, followed by the addition of a tertiary amine, e.g., diisopropylethyl amine. The reaction is stirred at between 5° and 35° C. for between 10 and 60 min to give an active T-CA linker.

In the second preferred activating procedure, the T-CA is treated with a phosgene equivalent (approx. 1.1 equivalent), e.g., 4-nitrophenylchloroformate, and a tertiary amine (approx. 1.1 equivalent), e.g., diisopropylethylamine, in an aprotic solvent, e.g., pyridine, at between 0° and 25° C. for between 10 min and 2 hrs to give the active T-CA linker.

Finally, to attach the active T-CA linker to a solid substrate having an amino-terminated linker, e.g., an aminoalkyl solid substrate, e.g., aminopropyl CPG, aminopropyl polystyrene, aminoalkylpolyethyleneglycol polystyrene, and the like, is added to the active T-CA linker and allowed to react at between 5° and 40° C. for between 1 and 10 hrs with occasional shaking or swirling of the reaction vessel. The derivatized solid support product is then filtered and washed in an organic solvent, e.g., methylene chloride, treated with a capping reagent (1:1:1 v/v/v acetic anhydride:N-methylimidazole:lutidine) for between 10 min and 2 hrs, filtered, washed with an organic solvent, and dried under vacuum to give the solid support reagent of Formula I as a white solid.

B. Alternative convergent synthesis of the $X_1$-containing solid support of Formula I:

The following is a preferred alternative generalized synthesis method for the compounds of Formula I. A diol as above (1 to 5 equivalents) and a tertiary amine (1.1 equivalents), e.g., triethylamine, are dissolved in an aprotic organic solvent, e.g., methylene chloride, and an acid-labile alcohol protecting reagent (1 equivalent), e.g., dimethoxytritylchloride, is added and stirred at between 0° and 25° C. for between 10 min and 5 hrs. The solution is washed with water and dried over sodium sulfate to give a monoprotected diol.

The monoprotected diol is then transformed to an active linker and attached to an aminoalkyl solid substrate similar to the T-CA in Method A above to give a T-linker support.

The T-linker support is then deprotected with acid, e.g., trichloroacetic acid in methylene chloride, at between 10° and 30° C. for between 1 and 30 min, washed with an organic solvent, e.g., methylene chloride, and dried, resulting in an alcohol-linker support.

The alcohol linker support is treated with a phosgene equivalent, e.g., 4-nitrophenylchloroformate, and a tertiary amine, e.g., diisopropylethylamine, in an aprotic organic solvent, e.g., pyridine, methylene chloride, acetonitrile, and the like, at between 10° and 30° C. for between 5 and 60 min. The support is then washed with an aprotic organic solvent, e.g., methylene chloride, to give a carbonate linker support.

The carbonate linker support is then treated with a T-amine (see Method A above) in a basic organic solvent, e.g., pyridine in acetonitrile, triethylamine in methylene chloride, and the like, at between 10° and 30° C. for between 10 min and 2 hrs. The support is washed with an aprotic organic solvent, e.g., methylene chloride, treated with a polynucleotide synthesis capping reagent (see Method A above) for between 10 min and 2 hrs, washed with an aprotic organic solvent, and dried to give the solid support of Formula I.

C. Synthesis of the $X_2$-containing solid support of Formula II:

The following is a preferred generalized synthesis method for the compounds of Formula II. The starting material is a $X_2$ linker defined by the formula:

wherein Z" is a precursor to Z and the other variable elements are as indicated above.

If the $X_2$ linker contains an amine, alcohol, or thiol, it is first protected with a non-base labile and non-acid labile protecting group, e.g., benzyl or silyl. Protocols for use of these and other applicable protecting groups can be found elsewhere, e.g., Greene and Wuts, Protective Groups in Organic Synthesis, 2nd Edition (John Wiley, New York, 1991).

The $X_2$ linker is then converted to an alcohol by treating with a strong base (2 equivalents), e.g., lithium diisopropylamide, sodium hydride, and the like, in a dry polar aprotic solvent, e.g., dimethylformamide, with stirring under argon. A ketone or aldehyde (1 equivalent) in a dry polar aprotic solvent is then added dropwise at between −40° and 0° C., the reaction is stirred at between −40° and 25° C. for between 10 min and 2 hrs, the reaction is quenched with water and concentrated by evaporation under vacuum. The residue is then dissolved in a water immiscible solvent, e.g., ethyl acetate, ether, methylene chloride, and the like, washed with water, dried over sodium sulfate, and concentrated under vacuum to give an alcohol linker defined by the formula:

wherein the variable elements are as indicated above.

The alcohol linker is then activated according to the above second preferred activating procedure for the active T-CA linker in Method A above to give the activated alcohol linker.

The T-amine (1 equivalent) and a tertiary amine (1 equivalent), e.g., diisopropylethylamine, is added and stirred at between 0° and 25° C. for between 10 min and 2 hrs. The solvent is evaporated under vacuum and the residue is dissolved in a water immiscible solvent, e.g., ethyl acetate. The solution is washed with water and dried over sodium sulfate. The solvent is then evaporated under vacuum to give the T-carbamate linker.

If the product contains a benzyl-protected amine, alcohol, or thiol, it is deprotected by hydrogenolysis, e.g., using hydrogen in combination with a palladium catalyst. Alternatively, if the product contains a silyl-protected amine, alcohol, or thiol, it is deprotected by treatment with a fluoride reagent, e.g., tetrabutylammonium fluoride.

If the T-carbamate linker is an amine, alcohol or thiol, then it can be activated as described above for the active T-CA linker in Method A. If the T-carbamate linker is a carboxylic or sulfonic acid, then it can be activated by treatment with a HOBT/HBTU reagent as described above. The resulting activated T-carbamate linker is then reacted with an aminoalkyl solid substrate as above to give the solid support shown in Formula II.

IV. UTILITY:

A preferred utility of the solid support of the present invention is in the synthesis of polynucleotides containing a nitrogen atom located at its 3'-end. Detailed descriptions of the chemistry used to form polynucleotides are provided elsewhere, e.g., Caruthers et al., U.S. Pat. No. 4,458,066; Caruthers et al., U.S. Pat. No. 4,415,732; Caruthers et al., Genetic Engineering, 4: 1–17 (1982); Users Manual Model 392 and 394 Polynucleotide Synthesizers, pages 6-1 through 6-22, Applied Biosystems, Part No. 901237 (1991). Accordingly, these references are incorporated by reference for those descriptions.

The phosphoramidite method of polynucleotide synthesis is the preferred method because of efficient and rapid coupling and the stability of the starting materials. The synthesis is performed with the growing polynucleotide chain attached to a solid substrate, so that excess reagents, which are in the liquid phase, can be easily removed by filtration, thereby eliminating the need for purification steps between cycles.

The following briefly describes the steps of a typical polynucleotide synthesis. The first step of the synthesis cycle is treatment of the solid support with acid to remove the hydroxyl protecting group, freeing the hydroxyl for the subsequent coupling reaction. A activated intermediate is then formed by simultaneously adding the phosphoramidite nucleoside monomer and a weak acid, e.g., tetrazole, and the like, to the reaction. The weak acid protonates the nitrogen of the phosphoramidite forming a reactive intermediate. This intermediate is so reactive that addition is complete within 30 s. The next step, capping, terminates any polynucleotide chains that did not undergo addition. Capping is preferably done with acetic anhydride and 1-methylimidazole. Finally, the internucleotide linkage is converted from the phosphite to the more stable phosphotriester. Iodine is used as the preferred oxidizing agent and water as the oxygen donor. After oxidation, the hydroxyl protecting group is removed with a protic acid, e.g., trichloroacetic acid or dichloroacetic acid, and the cycle is repeated until chain elongation is complete. After synthesis, the polynucleotide chain is cleaved from the support using a base, e.g., ammonium hydroxide. Ammonia treatment also removes the cyanoethyl phosphate protecting groups. Finally, the protecting groups on the exocyclic amines of the bases are removed by treating the polynucleotide solution in ammonium hydroxide at an elevated temperature, e.g., 55° C.

It will be apparent to those skilled in the art of polynucleotide synthesis that the present invention can also be used in conjunction with other synthetic methods, e.g., hydrogen phosponate or phosphotriester chemistries.

V. EXAMPLES

The following examples are intended to illustrate the preparation and application of the solid support reagents of the present invention. The values of the parameters used are only intended to exemplify the invention and are not to be considered limitations thereof.

Example 1

Synthesis of N-trifluoroacetyl-6-amino-1-hexanol 6-amino-1-hexanol (179 g) (Aldrich Chemical Company, Inc., Milwaukee, Wis.) was dissolved in methanol (358 ml) and ethyltrifluoroacetate (239 g) (Aldrich) was added dropwise to the solution over a period of 20 min. After stirring the reaction for 2.5 hrs, the solvent was removed under vacuum and the residue was dissolved in methylene chloride (250 ml), whereupon the solution was washed with water (3×300 ml) and a saturated sodium chloride solution (200 ml), and dried over sodium sulfate. Finally, the solvent was removed under vacuum giving a white solid (299 g).

Thin layer chromatography (TLC) Analysis: A TLC plate (Silica Gel GF, 250 μm thickness, 10×20 cm scored plates, Analtech, Inc., Newark Del.) was developed with 100% ethylacetate and stained with 5% phosphomolybdic acid in isopropyl alcohol. The $R_f$ of the 6-amino-1-hexanol and the N-trifluoroacetyl-6-amino-1-hexanol was 0 and 0.25, respectively.

Example 2

Synthesis of 1-0-(4,4'-dimethoxytrityl)-N-trifluoroacetyl-6-aminohexane

The N-trifluoroacetyl-6-amino-1-hexanol (10 g) from Example 1 and diisopropylethylamine (12.1 g) (Aldrich) were dissolved in methylene chloride (100 ml), ice-cooled to 5° C. and dimethoxytritylchloride (17.5 g) (Aldrich) was added to the cooled mixture. The mixture was stirred overnight (15 hr) during which the temperature was maintained at 5° C. for the first hour then allowed to rise to room temperature thereafter. Methylene chloride (100 ml) was added and the mixture was washed with a saturated sodium bicarbonate solution (100 ml) followed by a saturated sodium chloride solution (100 ml). The mixture was then dried over sodium sulfate and the solvent was removed under vacuum to give the desired product (29 g).

TLC Analysis: A TLC plate (same type as above) was developed with 50% ethyl acetate 1% triethylamine in hexane. The $R_f$ of the 1-0-(4,4'-dimethoxytrityl)-N-trifluoroacetyl- 6-aminohexane was 0.9.

Example 3

Synthesis of 1-0-(4,4'-dimethoxytrityl)-6-aminohexane

The 1-0-(4,4'-dimethoxytrityl)-N-trifluoroacetyl-6-aminohexane (20.9 g) from Example 2 was dissolved in methanol (100 ml), ice-cooled, and 4N sodium hydroxide was added (16.6 ml). The reaction was allowed to warm to room temperature, heated to 50° C. for 10 min using a heat gun, then stirred overnight (15 hrs) at room temperature. The methanol was removed under vacuum and the residue was mixed with water (100 ml) and ethyl acetate (150 ml). The organic layer was then washed with saturated aqueous sodium chloride (2×100 ml) and dried over sodium sulfate. The solvent was removed under vacuum to give the product as an oil (16.9 g).

Example 4

Synthesis of the carbamate adduct of 1-0-(4,4'-dimethoxytrityl)-6-aminohexane and 2,2'-sulfonyldiethanol Prior to the synthesis of the carbamate adduct of 1-0-(4, 4'-dimethoxytrityl)-6-aminohexane and 2,2'-sulfonyldiethanol, 2,2'-sulfonyldiethanol (Aldrich) was dried using the following procedure. 2,2'-sulfonyldiethanol (200 g of a 65% aqueous solution) was mixed with acetonitrile (200 ml), the mixture was distilled, and distillate was collected (240 ml) over a boiling point range of 70° C. to 90° C. The still pot was cooled to room temperature, additional acetonitrile was added (200 ml), the distillation process was repeated, and additional distillate was collected (270 ml). The distillation head was then replaced by a Stark trap, toluene (150 ml) was added, and the mixture was brought to reflux. After 3 hrs of trapping, water was recovered (12 ml), and the solvent removed under vacuum to give a viscous oil (105 g).

The dried 2,2'-sulfonyldiethanol (14.7 g) was then dissolved in tetrahydrofuran (100 ml) and stripped to dryness by rotary evaporation. The residue was dissolved in pyridine (100 ml) and diisopropylethylamine (12.3 g) under argon and cooled to approximately 10° C. using an ice bath, after which 4-nitrophenylchloroformate (9.6 g) (Aldrich) was added to the stirring solution and the reaction was allowed to warm to approximately 25° C. After 45 min, the reaction was cooled to 15° C. and the 1-0-(4,4'-dimethoxytrityl)-6-aminohexane (5 g) from Example 3 was added. After 5 min, the reaction was quenched with potassium carbonate (50 ml of a 5% aqueous solution). After 5 min, the solvent was removed under vacuum, the residue was dissolved in ethylacetate (150 ml) and extensively washed with water (2×200 ml each), potassium carbonate (2×100 ml each of a 5% aqueous solution), cold sodium hydroxide (8×100 ml each of a 0.5N aqueous solution), and saturated sodium chloride (2×100 ml each). The organic layer was then dried over sodium sulfate and the solvent removed under vacuum to give the product as an oil (7.9 g).

TLC Analysis: A TLC plate (same type as above) was developed with 5% methanol and 1% triethylamine in methylene chloride. The $R_f$ of the 1-0-(4,4'-dimethoxytrityl)-6-aminohexane and the carbamate adduct of 1-0-(4,4'-dimethoxytrityl)- 6-aminohexane and 2,2'-sulfonyldiethanol (hereinafter referred to as the carbamate adduct) was 0.2 and 0.4, respectively.

The crude carbamate adduct was purified by silica gel chromatography (column dimensions: 5.5 cm internal diameter and 8 cm length). The silica gel G60 was pretreated with an ethylacetate-triethylamine-hexane solvent system (50% ethyl acetate and 0.5% triethylamine in hexane) prior to the separation. The crude carbamate adduct was dissolved in ethylacetate-hexane solvent (50% ethyl acetate in hexane), loaded onto the pretreated column, and eluted with ethylacetate-hexane (50% ethyl acetate in hexane), ethyl acetate, then by methanol-ethyl acetate (10% methanol in ethyl acetate). Ten fractions were collected, and each fraction was analyzed by TLC (see immediately below for TLC conditions) and the appropriate fractions were combined to give the product as an oil (4.3 g).

TLC Analysis: A TLC plate (same type as above) was developed with 0:5% triethylamine in ethyl acetate. The $R_f$ of the carbamate adduct was approximately 0.3.

Example 5

Synthesis of the succinyl ester of the carbamate adduct of 1-0-(4,4'-dimethoxytrityl)-6-aminohexane and 2,2'-sulfonyldiethanol The carbamate adduct (2.0 g) from Example 4 and 4-dimethylaminopyridine (0.49 g) (Aldrich) were dissolved in methylene chloride (20 ml) under argon, and succinic anhydride (0.41 g) was added to the stirring solution at room temperature. After 5 min, additional methylene chloride was added (100 ml) and the solution was washed with cold citric acid (5×100 ml each of a 10% aqueous solution of citric acid) and saturated sodium chloride solution (2×100 ml each). The washed solution was dried over sodium sulfate and the solvent was removed under vacuum to give the product as an oil (2.1 g).

TLC Analysis: A TLC plate (same type as above) was developed with 5% methanol and 0.5% triethylamine in methylene chloride. The $R_f$ of the carbamate adduct was 0.4 and the $R_f$ of the succinyl ester of the carbamate adduct (hereinafter referred to as the succinyl ester) was 0.3.

The crude succinyl ester was purified by silica gel chromatography (column dimensions: 5.5 cm internal diameter and 8 cm length). The silica gel G60 was pretreated with a methanol-triethylamine-methylene chloride solvent system (1% methanol and 0.5% triethylamine in methylene chloride) prior to the separation. The crude succinyl ester was dissolved in a methylene chloride-methanol solvent (1% methanol in methylene chloride), loaded onto the column, and eluted with a three-step solvent gradient (200 ml of 1% methanol and 0.5% triethylamine, 200 ml of 5% methanol and 0.5% triethylamine, and 150 ml of 15% methanol and 0.5% triethylamine, each in methylene chloride). Eighteen fractions were collected, and each fraction was analyzed by TLC (see immediately below for TLC conditions). The appropriate fractions (fractions 8–13) were combined and the solvent removed under vacuum to give the product as an oil (1.32 g).

TLC Analysis: A TLC plate (same type as above) was developed with 5% methanol and 0.5% triethylamine in methylene chloride. As before, the $R_f$ of the succinyl ester was 0.3.

Example 6

Attaching the succinyl ester to 3-aminopropyl controlled pore glass forming the 3'-aminolinker support The succinyl ester (0.4 g) from Example 5 was dissolved in dimethylformamide (10 ml) under argon, and an equimolar solution of 1-hydroxybenzotriazole (HOBT) and 2-(1H-benzotriazol-1-yl)-1,1,3,3,-tetramethyluronium (HBTU) (1.14 ml of a 0.45M solution in dimethylformamide) (Applied Biosystems Division of the Perkin Elmer Corporation, Foster City, Calif. (ABI)) was added to the stirring solution, followed by the addition of diisopropylethylamine (0.14 g). After 15 min at room temperature, 3-aminopropyl-CPG (5.58 g of material having a loading of 40 μmole per gram)(ABI) was added to the stirring solution, the stirring was stopped, and the reaction was allowed to proceed for 2.5 hrs with occasional gentle swirling. The slurry was transferred to a medium-grit fritted funnel where the CPG support was washed with methylene chloride (5×20 ml), treated with a capping reagent (10 ml 0.5M N-methylimidazole in tetrahydrofuran and 10 ml 10% acetic anhydride 10% 2,6-lutidine in tetrahydrofuran), and allowed to stand for 30 min. The solution was then removed and the CPG was washed with methylene chloride (5×20 ml), then dried under vacuum to give a white solid (5.64 g).

Example 7

Synthesis of a 3'-aminohexyl polynucleotide using the solid support of the present invention Synthesis of a 3'-amino polynucleotide was performed on an Applied Biosystems 394 polynucleotide synthesizer using standard protocols and reagents (ABI). A brief description of the chemistry used by the 394 polynucleotide synthesizer is provided above in the section IV titled Utility. The solid support used in the synthesis was that whose synthesis is described in Examples 1–6 (32 mg). The base sequence of the polynucleotide was 5'-AGC TAG CT-3'. The product was cleaved off of the synthesis support with the terminal trityl group still attached, and was determined to be approximately 80% pure by HPLC analysis.

Example 8

Attaching a fluorescent dye to a 3'-aminohexyl polynucleotide

The crude polynucleotide (20%) from Example7 in 0.1M triethylammoniumacetate, pH 7 (100 μl), was added to a solution of 6-carboxy-fluorescein-N-hydroxysuccinimide ( 6-FAM) ester (1 mg in 100 μl dimethyl formamide) (Research Organics, Inc., Cleveland, Ohio), followed by the addition of a 1M NaHCO$_3$/Na$_2$CO$_3$ pH 9.0 solution (100 μl). The solution was vortexed and allowed to stand at room temperature for 30 min. The mixture was then applied to a PD-10 gel filtration column (Pharmacia, Piscataway, N.J.) and a single fraction was collected (1 ml fraction collected after the elution of a 2.5 ml void volume) to give 5'-AGCTAGCT-3'-aminohexyl-6-FAM.

Although the present invention has been described in considerable detail with reference to certain preferred versions thereof, other versions are possible. Those skilled in the art of chemistry will understand that there are many variations of the above support reagents, and methods for synthesis of the above support reagents, that fall within the preview of the present invention.

What is claimed is:

1. A solid support reagent for the synthesis of polynucleotides containing a nitrogen group at the 3'-end, the solid support reagent having the structure:

wherein:

T is an acid-cleavable hydroxyl protecting group;

Q is a linker for connecting nitrogen and oxygen;

$R_1$ is a nitrogen substituent;

$R_2$ through $R_4$ are separately hydrogen or lower alkyl;

Y is an atom which is electronegative with respect to carbon;

$X_1$ is a moiety which is electronegative with respect to carbon;

Z is a bond or spacer arm; and

W is a derivatized solid synthesis support capable of linking to Z.

2. A compound according to claim 1 wherein T is 4,4'-dimethoxytrityl, monomethoxytrityl, α-naphthyldiphenylmethyl, or tri(p-methoxyphenyl)methyl.

3. A compound according to claim 1 wherein T is 4,4'-dimethoxytrityl.

4. A compound according to claim 1 wherein Q is lower alkyl; or when in combination with an adjacent oxygen lower alkylene oxide; or when in combination with a nitrogen of the solid support reagent, Q is amide, carbamate, sulfonamide, or urea.

5. A compound according to claim 1 wherein Q is lower alkyl or lower alkylene oxide.

6. A compound according to claim 1 wherein $R_2$ through $R_4$ is hydrogen.

7. A compound according to claim 1 wherein Y is oxygen or sulfur.

8. A compound according to claim 1 wherein Y is oxygen.

9. A compound according to claim 1 wherein $X_1$ is sulphonyl, carbonyl, sulfoxide, perfluoro lower alkyl, or sulfonyl-, carbonyl-, sulfoxide, nitro-, cyano-, or perfluoro lower alkyl-substituted aryl.

10. A compound according to claim 1 wherein $X_1$ is sulphonyl, carbonyl, sulfoxide.

11. A compound according to claim 1 wherein Z is, in combination with a terminal nitrogen of the solid synthesis support derivatized with an amino-terminated linker, carbamate, urea, amide, sulfonamide, or a group of the formula:

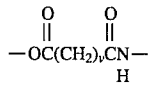

wherein v is an integer between 0 and 20.

12. A compound according to claim 1 wherein W is CPG derivatized with an amino-terminated linker.

13. A compound according to claim 1 wherein W is porous polystyrene derivatized with an amino-terminated linker.

14. A solid support reagent for the synthesis of polynucleotides containing a nitrogen group at the 3'-end, the solid support reagent comprising a compound of the formula:

wherein:

T is an acid-cleavable hydroxyl protecting group;

Q is a linker connecting the nitrogen and oxygen;

$R_1$ is a nitrogen substituent;

$R_2$ and $R_3$ are separately hydrogen or lower alkyl;

Y is an atom which is electronegative with respect to carbon;

$X_2$ is a moiety which is electronegative with respect to carbon;

Z is a bond or spacer arm; and

W is a derivatized solid synthesis support capable of linking to Z.

15. A compound according to claim 14 wherein T is 4,4'-dimethoxytrityl, monomethoxytrityl, α-naphthyldiphenylmethyl, or tri(p-methoxyphenyl)methyl.

16. A compound according to claim 14 wherein T is 4,4'-dimethoxytrityl.

17. A compound according to claim 14 wherein Q is lower alkyl; or when in combination with an adjacent oxygen lower alkylene oxide; or when in combination with a nitrogen of the solid support reagent, Q is amide, carbamate, sulfonamide, or urea.

18. A compound according to claim 14 wherein Q is lower alkyl or lower alkylene oxide.

19. A compound according to claim 14 wherein $R_2$ and $R_3$ are hydrogen.

20. A compound according to claim 14 wherein Y is oxygen or sulfur.

21. A compound according to claim 14 wherein Y is oxygen.

22. A compound according to claim 14 wherein $X_2$ is sulphonyl, carbonyl, sulfoxide, cyano, perfluoro lower alkyl, or sulfonyl-, carbonyl-, sulfoxide, nitro-, cyano-, or perfluoro lower alkyl-substituted aryl.

23. A compound according to claim 14 wherein $X_2$ is sulphonyl, carbonyl, or cyano.

24. A compound according to claim 14 wherein Z is, in combination with a terminal nitrogen of the solid synthesis support derivatized with a nitrogen-terminated linker, carbamate, urea, amide, sulfonamide, or a group of the formula:

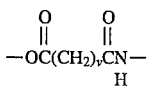

wherein v is an integer between 0 and 20.

25. A compound according to claim 14 wherein W is CPG derivatized with an amino-terminated linker.

26. A compound according to claim 14 wherein W is porous polystyrene derivatized with an amino-terminated linker.

* * * * *

UNITED STATES PATENT AND TRADEMARK OFFICE
CERTIFICATE OF CORRECTION

PATENT NO. : 5,552,471
DATED : September 3, 1996
INVENTOR(S) : Sam L. Woo and Steven Fung It is certified that error appears in the above-indentified patent and that said Letters Patent is hereby corrected as shown below:

Title page:
Other Publications, the Gao reference, delete "Tetrahedran" and insert --Tetrahedron--.

Abstract, line 8 of text, delete "4,4'-dimethoxytritil", and insert --4,4'-dimethoxytrityl--.

Abstract, line 16 of text, delete "amino-dirivitized", and insert --amino-derivatized--.

Column 5, line 53, delete "derivitization", and insert --derivatization--.

Column 11, line 26, delete "phosponate", and insert --phosphonate--.

Column 11, line 60; column 12, lines 11, 16, 18-19, 34, 38, 60; and column 13, lines 7, 8, 34, delete "aminohexane", and insert --aminolhexanol--.

Signed and Sealed this

Eleventh Day of February, 1997

Attest:

BRUCE LEHMAN

Attesting Officer

Commissioner of Patents and Trademarks